United States Patent [19]

Brignola et al.

[11] Patent Number: 4,479,578
[45] Date of Patent: Oct. 30, 1984

[54] SINGLE BARREL TWO-COMPARTMENT MEDICAMENT CONTAINER ASSEMBLY

[75] Inventors: Dominic J. Brignola, Phoenixville; Homer J. Brown, Oreland; Caroll S. Sutryn, Oaks; Ralph Walters, Perkiomenville, all of Pa.

[73] Assignee: The West Company, Phoenixville, Pa.

[21] Appl. No.: 252,588

[22] Filed: Apr. 9, 1981

[51] Int. Cl.³ .................. B65D 81/32; B65D 51/26
[52] U.S. Cl. ................................ 206/221; 215/6; 604/92
[58] Field of Search ............... 206/219, 220, 221, 222; 215/6; 128/272, 218 M

[56] References Cited

U.S. PATENT DOCUMENTS 2,689,566  9/1954  Lockhart .................. 128/272
2,717,601  9/1955  Brown ..................... 128/272
2,787,268  4/1957  Greenspan ................ 206/221

Primary Examiner—William T. Dixson, Jr.
Attorney, Agent, or Firm—Eugene E. Renz, Jr.

[57] ABSTRACT

A single barrel two compartment assembly for medicaments comprising an elongated cylindrical hollow barrel having a normally sealed discharge end, a bypass plunger made of a pliable resilient material having a forward section of a diameter slightly greater than the diameter of the barrel, means defining a seat in the bypass plunger, a plunger rod having a tip engageable in said seat for actuating said bypass plunger axially in said barrel and seal means for sealing the open end of the said barrel remote from said discharge end, said bypass plunger normally dividing said barrel into a first compartment to one side of the bypass plunger for a powder medicament and a diluent compartment on the opposite side of said bypass plunger, actuation of said bypass plunger in one direction creating internal diluent pressure whereby said diluent bypasses the periphery of said plunger to mix with said powder medicament.

8 Claims, 17 Drawing Figures

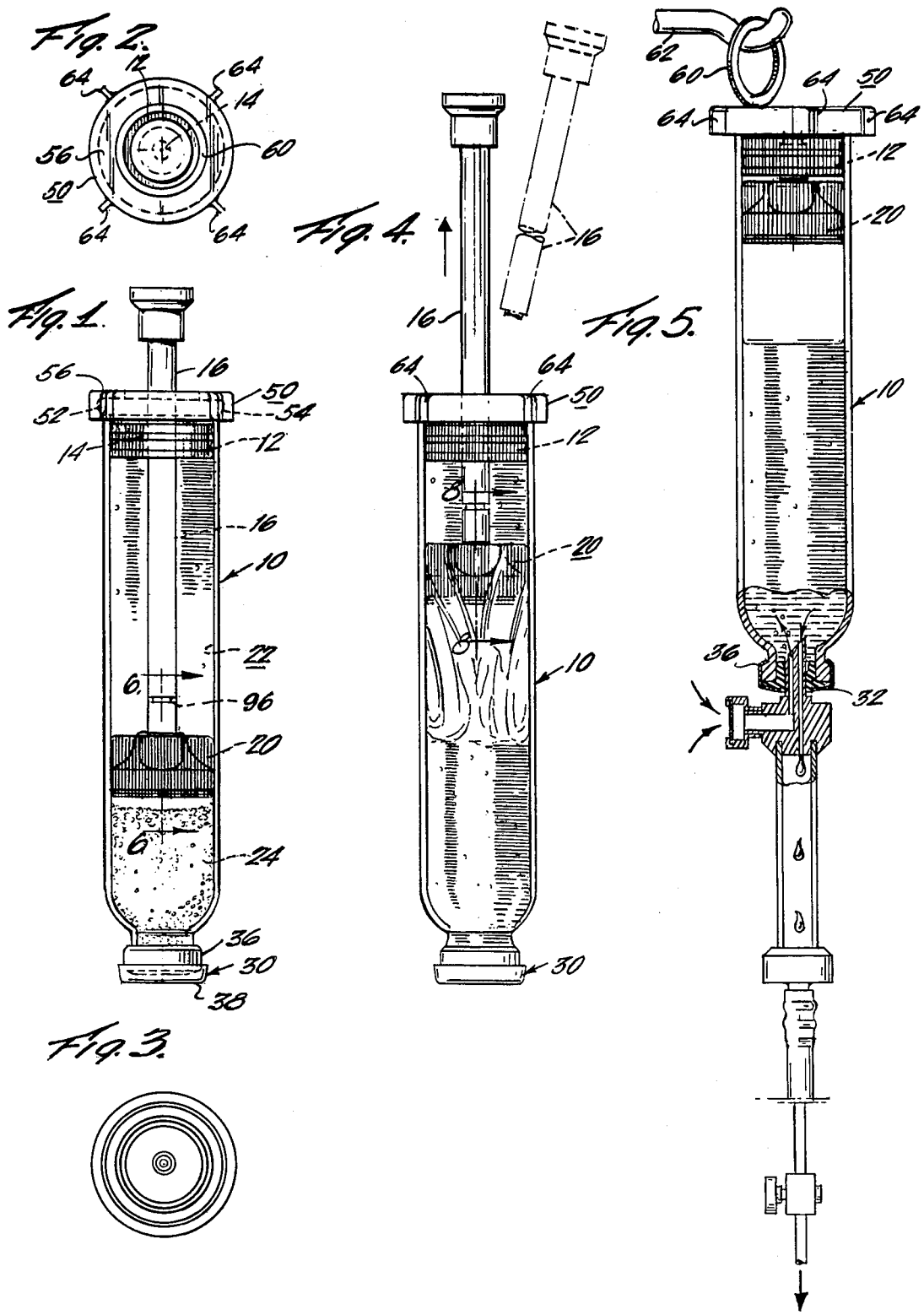

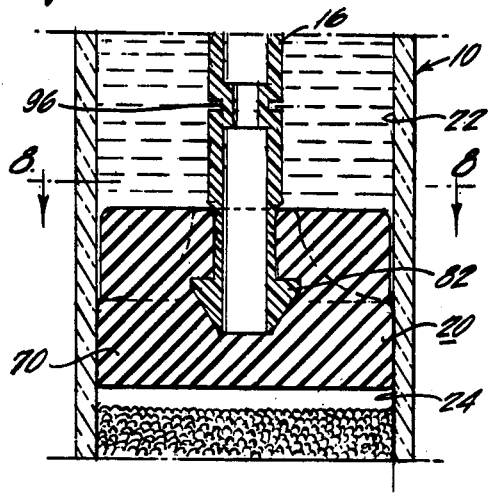
Fig. 6. (STORAGE)
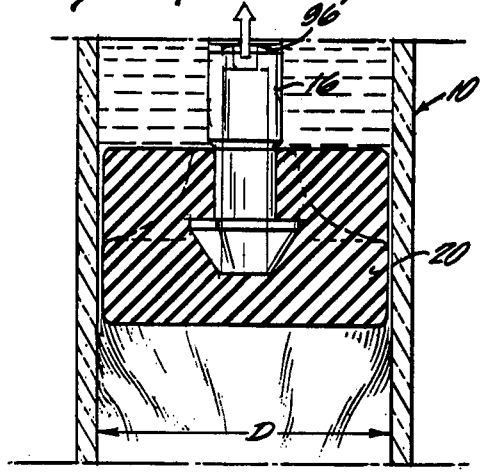
Fig. 7. (TRANSFER)
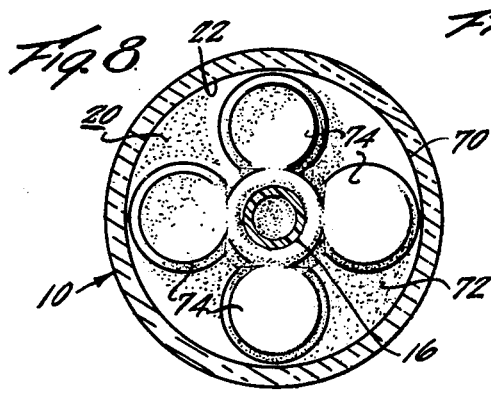
Fig. 8.
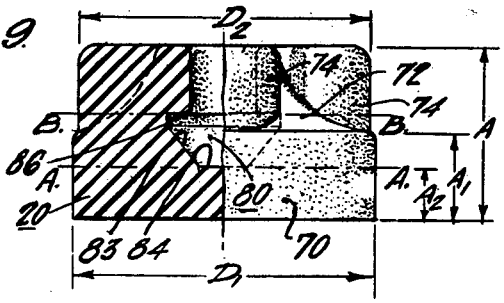
Fig. 9.
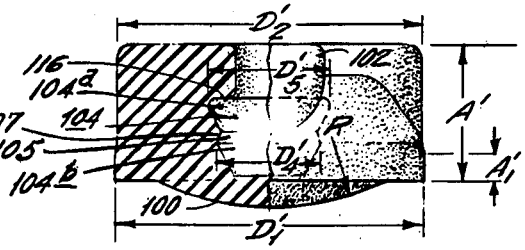
Fig. 10.
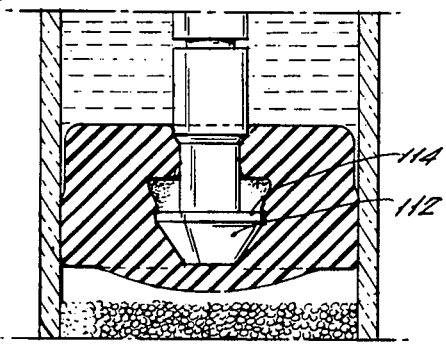
Fig. 11.
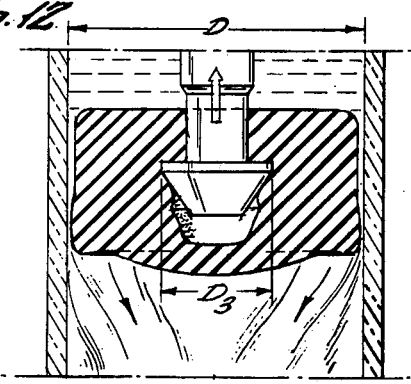
Fig. 12.

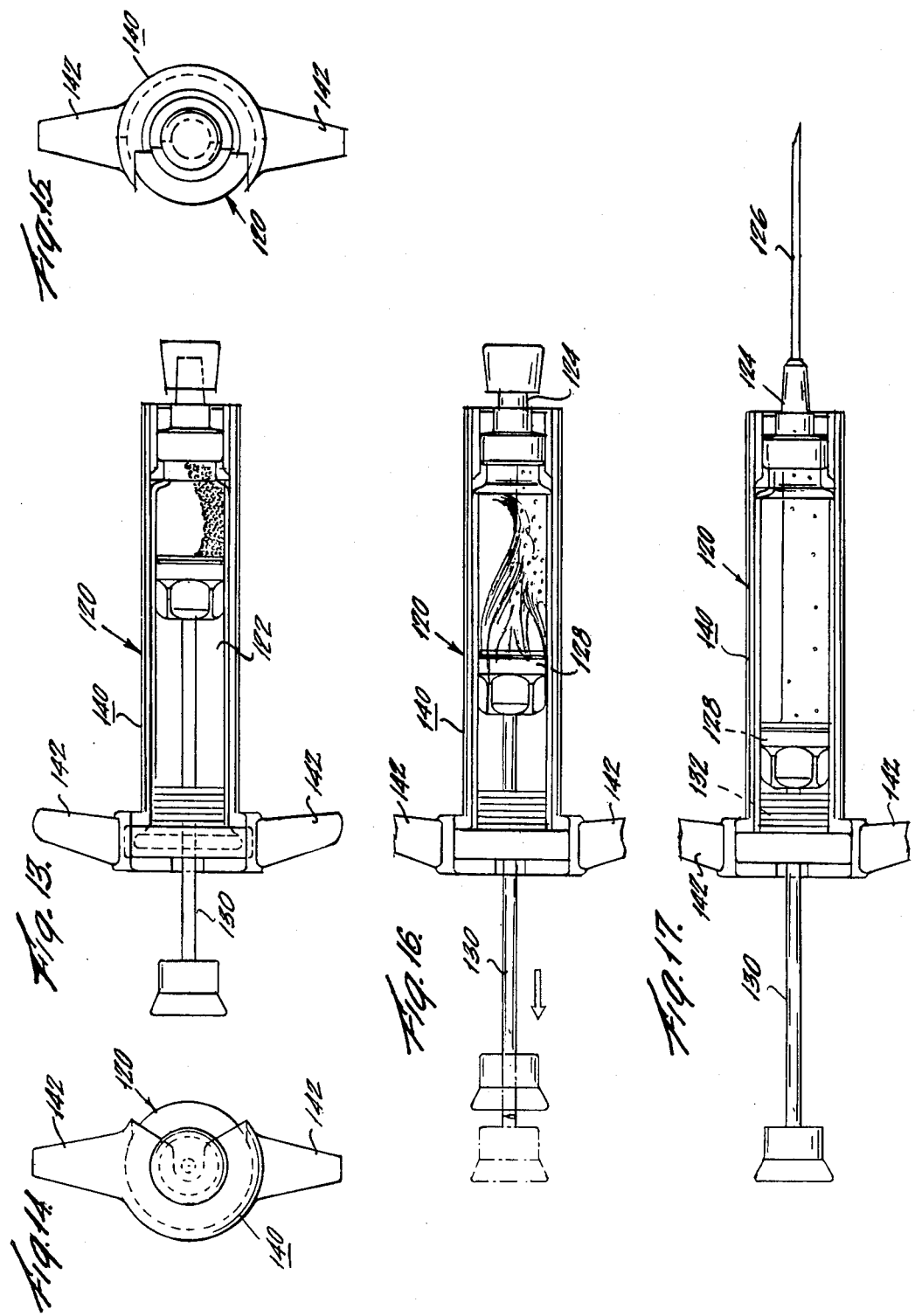

even after activation. To this end, the assembly includes an elongated barrel, a bypass piston slideably mounted in the barrel, and a plunger rod connected to the piston for movement of the bypass piston therein. The unit is easy to fill with the powder product and diluent. This is simply done by sealing the discharge end of the barrel, depositing the desired quantity of powder medicament into the bottom of the barrel and thereafter inserting the bypass plunger in the barrel to a predetermined depth just above the level of a powder medicament. The diluent is then added to fill the barrel above the bypass piston. The upper seal is then pressed in place and the assembly is ready for storage. When it is desired to mix the diluent and powder medicament, the plunger rod is simply withdrawn axially, whereby the diluent bypasses the plunger and the admixed product is now ready for use. Note that in this operation none of the elements of the assembly which are likely to be contacted by the user comes in contact with the diluent or powder product during reconstitution thereof. Furthermore, the bypass plunger is displaced by a fixed positive connection between the piston rod and bypass plunger and does not depend on displacement by build up of internal pressure as in the two compartment vials discussed above.

SINGLE BARREL TWO-COMPARTMENT MEDICAMENT CONTAINER ASSEMBLY

BACKGROUND AND SUMMARY OF THE INVENTION

The present invention relates to improvements in plural compartment containers for medicaments and the like and more specifically to that type of container adapted for temporarily isolating a compartment containing a solid pharmaceutical product from a compartment containing an aequeous solution for storage purposes and wherein the components may be readily admixed to use the medication.

Two compartment vials or containers wherein a medication and a solvent can be held in complete independence or isolation from each other until it is desired to use the medication are not new per se. Typical prior compartmented vials are illustrated for example, in Crankshaw, et al, U.S. Pat. Nos. 4,194,640, No. 4,089,432 and the Lockhart U.S. Pat. No. 2,869,745. These vials are generally of the same construction and comprise an hourglass shaped container made of glass having a movable stopper supported in the discharge end and a plug made of resilient material, such as rubber, frictionally force fitted in the constricted or reduced venturi center section of the container dividing the container into an upper chamber or compartment usually for the diluent or solvent and a lower chamber or compartment for the powder medicament. By this arrangement, the solvent and power medicament are isolated for good shelf life and now when it is desired to mix the two, the stopper in the discharge end is simply pressed inwardly to create internal pressure sufficient to displace the plug in the venturi of the container into the lower compartment to allow mixing of the solvent and powder medicament.

While these prior vial or container assemblies for medicaments are generally suitable for the purposes intended, there are nevertheless certain disadvantages and drawbacks which the present invention is designed to overcome. For example, it has been found that the center seal or plug is somewhat clumsy and difficult to assemble in place to provide the necessary hermetic seal between the diluent and the powder medicament compartments. Furthermore, because of the usually small size of this plug, and the variations and imperfections usually inherent in glass containers, the seal is usually not of a character to provide a good moisture-vapor barrier ensuring against breakdown of the product over an extended shelf life period. Furthermore, the stopper at the discharge end of the container has to be of a prescribed tight fit to ensure against leakage which would permit air bypass and thereby preclude displacement of the center plug when the outer stopper is pressed inwardly. Additionally in these prior assemblies, a portion of the outer stopper is exposed to the ambient atmosphere and may be contacted by the user. Thus when the stopper is displaced upon activation to a position where the medicament product may contact this portion of the stopper, there is the possibility of contaminating the medicament.

There are also prior syringe assemblies wherein the diluent and the powder medicament are maintained in separate isolated chambers for storage. These syringe assemblies typically comprise an outer barrel for the powder medicament and an inner barrel which telescopically fits into the outer barrel and has a plunger assembly with a rupturable diaphragm normally closing the open end thereof. When it is desired to activate the syringe, the plunger is pressed inwardly to rupture the diaphragm at the discharge end of the inner barrel and permit flow of diluent to the powder medicament in the outer barrel.

By contrast, the present invention provides a self-contained unit wherein the parts of the container or syringe contacting the diluent and powder medicament can be effectively sterilized and maintained in a sterile condition With the above in mind, it is an object of the present invention to provide a novel single barrel two compartment container assembly suitable for use in an intravenous administration set or as a syringe which is comprised of comparatively few parts and is fully effective in operation and use.

Another object of the present invention is to provide assembly wherein the diluent and powder medicament are maintained in a sterile environment prior to use and can be easily mixed in that same environment.

Still another object of the present invention is to provide a single barrel two compartment assembly for medicaments wherein the plunger arrangement ensures a positive seal providing an extended storage life and which is nevertheless relatively easily displaced to mix the contents when desired.

A further object of the present invention is to provide any single barrel two compartments arranged and comprised of relatively few parts which is simple and economical to manufacture and assemble.

BRIEF DESCRIPTION OF THE DRAWINGS

These and other objects of the present invention and the various details of the operation and construction thereof are hereinafter more fully set forth with reference to the accompanying drawings, wherein:

FIG. 1 is a side elevational view of an intravenous infusion set or assembly in accordance with the present invention;

FIG. 2 is a top plan view thereof;

FIG. 3 is a bottom plan view thereof;

FIG. 4 is a slide elevational view similar to FIG. 1 showing the plunger activated to a transfer position;

FIG. 5 is a side elevational view of the infusion set partly in section in an operative environment;

FIGS. 6 and 7 are enlarged sectional views taken on lines 6—6 and 7—7 of FIGS. 1 and 4 respectively;

FIG. 8 is a view of the bypass plunger taken on lines 8—8 of FIG. 6;

FIG. 9 is a side elevational view partly in section of the bypass plunger;

FIG. 10 is a side elevational view partly in section of a modified form of bypass plunger in accordance with the present invention;

FIG. 11 is a transverse sectional view through an assembly similar to FIG. 6 showing the bypass plunger of FIG. 10 in a storage position;

FIG. 12 is a sectional view of the bypass plunger of FIG. 10 with the parts disposed in a transfer position;

FIG. 13 is a side elevational view of a single barrel, two compartment syringe in accordance with the present invention with the parts disposed in a storage position;

FIGS. 14 and 15 are top and bottom plan views thereof respectively;

FIG. 16 is a view similar to FIG. 9 showing the plunger retracted for fixing the solvent in the powder medicament; and FIG. 17 shows the syringe assembly with the needle assembled for discharging the admixed medicament.

DESCRIPTION OF THE PREFERRED EMBODIMENTS

Referring now to the drawings and particularly to FIGS. 1-8 thereof, there is illustrated an intravenous (IV) infusion set in accordance with the present invention. As illustrated therein, the assembly includes an elongated generally tubular container, preferably made of glass designated by the numeral 10 which is sealed at its upper end by a ribbed plunger or seal 12 having a central opening 14 therein to accommodate a plunger rod 16 which mounts at its inner end a by-pass plunger 20 dividing the barrel compartment into an upper chamber 22 for diluent and a lower chamber 24 for a powder medicament. The discharge end of the barrel 10 is sealed by a closure assembly 30 consisting of a rubber stopper 32 having a punctuable diaphragm 34 and an outer cap 36 crimped under the finish at the discharge end to hold the closure in place and a removable cover member 38 connected to a disc detachably connected to the outer cap. The cover member 38 normally maintains the stopped in a sterile condition. However, the stopper can be exposed simply by pivoting the cover member which removes the central disc from the outer cap member to expose a portion of the stopper for piercing and access to the contents in the barrel. This closure assembly 30 is of a type shown in Ravn U.S. Pat. No. 3,193,128 entitled CONTAINER CLOSURE issued June 12, 1962.

The back plunger or rear seal is held in place by a snap cap 50 which fits over the upper end of the barrel and has an inwardly directed lower rib 52 which seats under an annular outwardly directed bead 54 at the upper end of the barrel. The cap 50 has an annular top 56 which projects radially inwardly beyond the inner diameter of the barrel to serve as a stop to retain the back plunger or seal in place when the bypass plunger is actuated rearwardly by the plunger rod to transfer and mix the container contents. The cap 50 also includes a ring-like loop 60 of a size to fit over the end of the plunger rod which can be pivoted into an upright position to support the assembly on a support bracket 62 adjacent the bed of a patient in the manner illustrated in FIG. 5. The bypass plunger 20 and rear seal 14 are preferably made of a pliable, resilient material such as rubber and the barrel 10 is preferably glass. The barrel may be polymerized to facilitate movement of the bypass plunger when actuating the assembly.

The sidewall of the snap cap 50 has a series of circumferentially spaced axial ribs 64 which project radially outwardly which serve as means limiting rolling movement of the assembly during permanent storage and if the barrel is placed temporarily on a flat surface such as a tray.

Considering now the structural details and arrangement of the bypass plunger and the mounting arrangement for the plunger rod, the bypass plunger as illustrated in FIGS. 7 and 8, comprises a disc-like forward or base section 70 which is of a larger diameter $D_1$ than the inner diameter $D$ of the barrel to effectively seal the chambers 22 and 24 during storage and provide a long shelf life, a rearwardly extending gradually tapering throat section 72 and a series of circumferentially spaced ribs 74 of generally arcuate cross section as shown in FIG. 8. In the present instance there are four ribs 74 equispaced circumferentially so that the outer side edge of opposing pairs of the ribs are spaced closely to the inner side wall of the barrel 10 and act as guide means preventing cocking of the bypass plunger 20 during actuation axially in the barrel. The distance $D_2$ between the outer sides of the opposing guide ribs 74 is equal to or slightly less than the inner diameter $D$ of the barrel. The bypass plunger 20 has a central cavity 80 therein defining a pocket or seat for the inner terminal end or tip 82 of the plunger rod. The seat as illustrated is frusto-conical with the conical side wall 83 converging toward the front face 80a of the bypass plunger. The base 84 of cavity 80 lies in a plane A—A approximately midway of the axial thickness of the forward section of the plunger and the top wall 86 of the seat lies in a plane B—B above the forward section 70. As illustrated, the tip 82 of the plunger rod is generally conical shape and has a maximum diameter greater than the largest diameter of the cavity 80 so that when the bypass plunger 20 is displaced forwardly in the barrel, the tip 82 expands the forward section 70 of the plunger radially to provide a tight seal with the barrel for extended shelf life. This expanding pressure is relieved slightly when the plunger rod is moved rearwardly during the mixing stroke to facilitate movement of the plunger and flow of the diluent around its periphery.

As illustrated, the plunger rod is a hollow elongated tubular member preferably made of a plastic material having a circumferentially extending groove 96 spaced from the tip of a predetermined distance above the bypass plunger when it is seated in place as illustrated in FIG. 6 to provide a breakaway location. Accordingly, when the bypass plunger has been fully retracted and the components mixed, the plunger can easily be fractured or separated at the groove simply by tilting it. Note that the breakaway point is slightly below the top face of the rear seal so that no jagged edges project beyond the rear seal and the assembly can be mounted on a support without interference from the plunger rod. Note also that the cross section of the plunger rod immediately behind the tip 82 is of reduced cross section as at 96 to fit snugly in the bypass plunger in the manner illustrated.

The diameter $D_1$ of the lower section 70 of the bypass plunger 20 is selectively sized in relation to the inner diameter D of the barrel to provide a good hermetic seal isolating the diluent and medicament for extended shelf life purposes and yet allows for relatively easy actuation of the bypass plunger rearwardly and flow of fluid around the plunger in the manner illustrated in FIG. 4 to achieve mixing of the components. The following is an example of typical dimensional relationships of parts of the assemblies for achieving this purpose.

| D | Barrel Inner Diameter | 1.110" ± .005" |
|---|---|---|
| $D_1$ | Bypass Plunger Base Section Diameter | 1.140" |
| $D_2$ | Distance Between Outer Faces of Ribs | 1.120" |
| A | Axial Height of Bypass Plunger | .660" ± .015" |
| $A_1$ | Axial Height of Bypass Plunger Base | .336" ± .012 |
| $A_2$ | Distance of Plunger Rod Seat Base From Lower Face of Bypass Plunger | .200" |

Consider now briefly, the use and operation of the single barrel, two compartment medicament infusion set or assembly. The flip-off closure 30 is applied to the reduced lower discharge end of the barrel 10 in a standard way simply by rolling the peripheral edge of the outer cap under the container finish. The powder medicament is then inserted into the open end of the barrel 10 and thereafter the bypass plunger 20 inserted in the barrel to a position slightly above the level of the powder medicament. The upper compartment or chamber 22 is then filled with diluent. The back plunger or rear seal 12 is then pressed into place and the overcap 50 simply snapped onto the top of the barrel. The assembly may then be stored. The overcap 50 as illustrated is provided with four circumferentially spaced ribs or protusions 64 which prevent rolling of the assembly either when it is stored or prior to use if it is placed on a flat planar surface such as a tray. As the bypass plunger 20 is actuated in a rearward direction, the diluent pressure buildup and also relaxation of the plunger rod tip 82 in its seat which may also be operative to reduce slightly the normal outward radial pressure of the plunger rod tip tending to press the lower section of the bypass plunger against the inner barrel wall permit bypass of the diluent about the periphery of the bypass plunger to the lower chamber 24 to mix with the powder medicament. Note that the plunger rod is now pulling on the upper wall 86 of the frusto-conical seat which is spaced upwardly from the top wall of the lower section 70 of the bypass plunger. When the plunger rod has been fully extended, it may be severed at the weakened juncture. The ring loop 60 is then pivoted upwardly so that the assembly can be suspended on a support near the patient as illustrated. The plastic cover is then removed to insert the transfer spike of the administrator set.

There is illustrated in FIGS. 10, 11 and 12 a modified bypass plunger construction in accordance with the present invention. In this instance, the plunger is generally dome shape configuration having a slightly outwardly dished front face 100 and a plurality of circumferential spaced guide ribs 102, in the present instance, four ribs which have outer side edges spaced slightly inwardly from the lower section of the dome. This configuration provides a slightly flexible outer peripheral edge portion which as described in more detail below, tends to contract on the transfer stroke for ease of moving the bypass plunger rearwardly to allow flow of the diluent around the piston during the mixing stroke and which in some applications such as in syringes, flexes outwardly to snugly engage the side wall of the barrel to ensure complete discharge of the contents of the unit when the bypass plunger is actuated forwardly to dispense the mixed medicament. The bypass plunger also has a centrally located generally frusto-conical seat 104 for the plunger rod tip which in this instance is of a double cone staggered configuration defining an upper seat section 104a and an lower seat section 104b connected by a juncture section 105 having a reversely tapered wall 107. The lower seat section 104b is aligned with the forward section of the bypass plunger and is of a maximum diameter $D_4'$ less than the diameter $D_3'$ of the plunger rod tip so that when the bypass plunger is moved forwardly in the barrel during assembly for example, the plunger rod tip presses the material of the plunger radially outwardly to provide a tight engagement with the barrel and provide an optimum moisture-vapor barrier isolating the powder chamber or compartment from the diluent compartment. Note that in the storage position the plunger rod tip seats firmly in the reversely tapered juncture section 105 defined by the tapered wall 107. Now when it is desired to activate the bypass plunger to mix the ingredients in each of the compartments, the plunger rod tip is moved axially rearwardly and is displaced to engage in the upper seat section 104a of the bypass plunger thereby relieving the radial expanding pressure on the plunger to facilitate actuation of the plunger in the barrel and permit flow of diluent around the peripheral edge of the bypass plunger. More specifically, the maximum diameter $D_5'$ of the upper seat section 104a of less than the diameter $D_3'$ of the plunger rod tip and the upper seat section 104a is located above the forward section of the bypass plunger. This arrangement, therefore, ensures a good tight fit of the bypass plunger in the barrel during storage for extended shelf life and minimizes the force required to actuate the bypass plunger rearwardly. The plunger rod tip as illustrated is also of conical shape 112 and of a dimension slightly larger than the lower seat section in the bypass plunger and a slightly smaller dimension than the upper seat section. Nevertheless, the dimensions are such so that the radial upper face 114 of the plunger rod normally engages against the radial top face 116 of the seat to ensure good contact when actuating the bypass plunger rearwardly to activate the assembly.

Even though the bypass plunger, plunger rod and barrel relationships may vary slightly, set forth below, is an example of the preferred dimensional relationships for a given sized bypass plunger and barrel assembly.

| D | Barrel Inner Diameter | 1.110" ± .005" |
|---|---|---|
| $D_1'$ | Bypass Plunger Base Section Diameter | 1.160" ± .008" |
| $D_2'$ | Distance Between Outer Faces of Ribs | 1.150" ± .008' |
| $D_3'$ | Plunger Rod Tip Diameter | .425" |
| $D_4'$ | Maximum Diameter Lower Seat Section | .375" |
| $D_5'$ | Maximum Diameter Upper Seat Section | .460" |
| R | Radius of Bypass | 1.000" |

| | -continued | |
|---|---|---|
| A' | Plunger Lower Face Axial Height of Bypass Plunger | .620" ± .020" |
| A₁' | Axial Height of Plunger Base or Lower Section | .127" |

There is illustrated in FIGS. 13–17 inclusive a single barrel two compartment syringe assembly in accordance with the present invention. The syringe assembly is broadly designated by the numeral 120 and comprises an elongated barrel 122, a fitting 124 at the discharge end thereof for attaching a needle 126, a bypass plunger 128 detachably connected to a plunger rod 130 and a seal 132 at the end of the barrel remote from the tip end. The bypass plunger may be of the construction and arrangement illustrated in the previously described embodiments and as illustrated in FIG. 9 normally separates the syringe barrel into a forward compartment for a powder medicament and a rearward compartment for a diluent or solvent. In the present instance, the syringe assembly is mounted in an elongated holder 140 having diametrically opposed radially projecting finger supports 142 for engagement by the fingers of the user to activate the syringe to mix the contents as well as discharge the contents into an IV administration system or directly into a patient. The holder as illustrated in FIG. 14 is open at one side to snap fit to the barrel and facilitate easy assembly and removal of the syringe barrel therein.

Consider briefly the operation of the syringe. As noted above, the parts of the syringe are in the relative position indicated in FIG. 9 for storage wherein the bypass plunger seals the chambers for an extended shelf life of the medicament. When it is desired to activate the syringe, the plunger rod is simply displaced rearwardly as illustrated in FIG. 12 whereby the diluent bypasses the periphery of the bypass plunger and enters the forward compartment to mix with the powder medicament. Note that during storage and the mixing operation, a seal plug 150 hermetically seals the discharge end of the hub assembly. When the contents have been fully mixed and the bypass plunger is in a fully rearward position, the seal plug 150 is simply removed and the syringe needle assembled. The hub and syringe needle may be a convential lure type fitting. Now when it is desired to discharge the contents, the plunger rod is simply pushed inwardly and as it is moved forward, the rear seal moves along with the bypass plunger to eliminate creation of the vacuum block.

While particular embodiments of the present invention has been illustrated and described herein, it is not intended to limit the invention and changes and modifications may be made therein within the scope of the following claims.

What is claimed is:

1. A single barrel two compartment assembly for medicaments comprising an elongated cylindrical hollow barrel having a substantially uniform diameter, a normally sealed discharge end, a bypass plunger made of a pliable resilient material having a forward section of a diameter slightly greater than the diameter of the barrel in a relaxed state, means defining a seat in the bypass plunger, a plunger rod having a tip engageable in said seat for actuating said bypass plunger axially in said barrel and seal means for sealing the open end of the said barrel remote from said discharge end, said bypass plunger normally dividing said barrel into a first compartment to one side of the bypass plunger for a powder medicament and a second diluent compartment on the opposite side of said bypass plunger, actuation of said bypass plunger toward said second compartment creating an increase in hydrostatic diluent pressure and relaxation of the sealing engagement of said plunger forward section and said bore of the barrel thereby permitting diluent to bypass the periphery of said plunger to mix with said powder medicament in said first compartment.

2. An assembly as claimed in claim 1 wherein said seat is of frusto-conical cross-section and wherein said plunger rod tip is of a frusto-conical configuration complementing said seat.

3. An assembly as claimed in claim 1 wherein said plunger rod is of reduced cross section adjacent to said tip so that it can be severed at this location when the bypass plunger has been actuated to a position remote from said discharge end to mix the contents of said assembly.

4. An assembly as claimed in claim 1 including a snap cap removably secured to said barrel opposite said discharge end including a plurality of circumferentially extending radially projecting ribs.

5. An assembly as claimed in claim 1 wherein said bypass plunger includes a first seat section having a maximum diameter smaller than the maximum diameter of said plunger rod tip and upper contiguous seat section of a maximum diameter slightly larger than the maximum diameter of said plunger rod tip.

6. An assembly as claimed in claim 1 wherein the outer face of said bypass plunger has a protruding arcuate projection.

7. An assembly as claimed in claim 1 including a series of circumferentially spaced ribs projecting rearwardly from the forward section of said bypass plunger and of a radial projection slightly less than the diameter of the forward section of the plunger to serve as guide means.

8. An assembly as claimed in claim 1 wherein said plunger rod tip acts as an expanding means in the normal position of said plunger pressing the forward section of the plunger into sealing engagement with the bore of the barrel and upon actuation of the plunger acts to elongate the resilient material of the plunger to permit bypass of diluent.

* * * * *